United States Patent
Srinivasan

(10) Patent No.: US 11,399,733 B2
(45) Date of Patent: Aug. 2, 2022

(54) ADVANCED SAFE INFANT MRI SYSTEM COMPRISING MRI COMPATIBLE INFANT WARMING MATTRESS

(71) Applicant: Advanced Imaging Research, Inc., Cleveland, OH (US)

(72) Inventor: Ravi Srinivasan, Beachwood, OH (US)

(73) Assignee: Advanced Imaging Research, Inc., Cleveland, OH (US)

( * ) Notice: Subject to any disclaimer, the term of this patent is extended or adjusted under 35 U.S.C. 154(b) by 352 days.

(21) Appl. No.: 16/649,781

(22) PCT Filed: Sep. 21, 2018

(86) PCT No.: PCT/US2018/052113
§ 371 (c)(1),
(2) Date: Mar. 23, 2020

(87) PCT Pub. No.: WO2019/060655
PCT Pub. Date: Mar. 28, 2019

(65) Prior Publication Data
US 2020/0275859 A1    Sep. 3, 2020

Related U.S. Application Data

(60) Provisional application No. 62/561,757, filed on Sep. 22, 2017.

(51) Int. Cl.
*A61B 5/055* (2006.01)
*G01R 33/31* (2006.01)
(Continued)

(52) U.S. Cl.
CPC .............. *A61B 5/055* (2013.01); *G01R 33/31* (2013.01); *G01R 33/3804* (2013.01); *G01R 33/3815* (2013.01); *A61B 2503/04* (2013.01)

(58) Field of Classification Search
CPC .... A61B 5/055; A61B 2503/04; G01R 33/31; G01R 33/3804; G01R 33/3815;
(Continued)

(56) References Cited

U.S. PATENT DOCUMENTS

2003/0184298 A1   10/2003   Heid et al.
2007/0232894 A1   10/2007   Feenan
(Continued)

FOREIGN PATENT DOCUMENTS

CN    102551978 A   *   7/2012
CN    204274760 U   *   4/2015
(Continued)

OTHER PUBLICATIONS

International Search Report from corresponding International Patent Application No. PCT/US2018/052113, dated Jan. 21, 2019.

*Primary Examiner* — G. M. A Hyder
(74) *Attorney, Agent, or Firm* — Kusner & Jaffe

(57) ABSTRACT

A pediatric magnetic resonance (MRI) system and sub-system are provided. The pediatric MRI system includes a magnet-gradient assembly, an RF shield-body coil assembly and a pediatric MRI sub-system. The pediatric MRI sub-system includes an infant warmer or isolette having a patient section for accommodating a patient. The infant warmer is positionable relative to the magnet-gradient-body coil assembly of the pediatric MRI system. The pediatric MRI sub-system also includes a warming mattress arranged within the patient section of the infant warmer. The infant warming mattress includes an interior space filled at least partially with a host medium and a conduction heating system at least partially arranged in the interior space to conduct heat to the interior space of the infant warming mattress. The pediatric MRI system also includes at least
(Continued)

one local radio frequency (RF) coil that is positionable within the patient section of the infant warmer.

23 Claims, 7 Drawing Sheets

(51) Int. Cl.
*G01R 33/38* (2006.01)
*G01R 33/3815* (2006.01)

(58) Field of Classification Search
CPC ....... G01R 33/34076; A61F 2007/0054; A61F 2007/0072; A61F 2007/0088; A61F 2007/0242; A61F 7/007; A61F 7/08; A61G 11/00
See application file for complete search history.

(56) References Cited

U.S. PATENT DOCUMENTS

| | | | |
|---|---|---|---|
| 2010/0137704 A1 | 6/2010 | Vij et al. | |
| 2015/0226817 A1* | 8/2015 | Pourrahimi | G01R 33/3815 324/309 |
| 2016/0206471 A1* | 7/2016 | Rapoport | A61M 16/105 |
| 2021/0007884 A1* | 1/2021 | Rapoport | G01R 33/3815 324/309 |

FOREIGN PATENT DOCUMENTS

| | | |
|---|---|---|
| JP | 2012-200407 A | 10/2021 |
| WO | WO 2016/153471 A1 | 9/2016 |

* cited by examiner

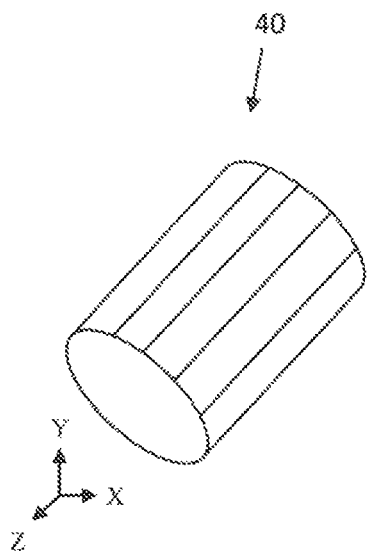
Figure 4A
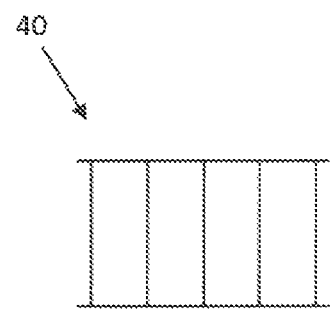
Figure 4B
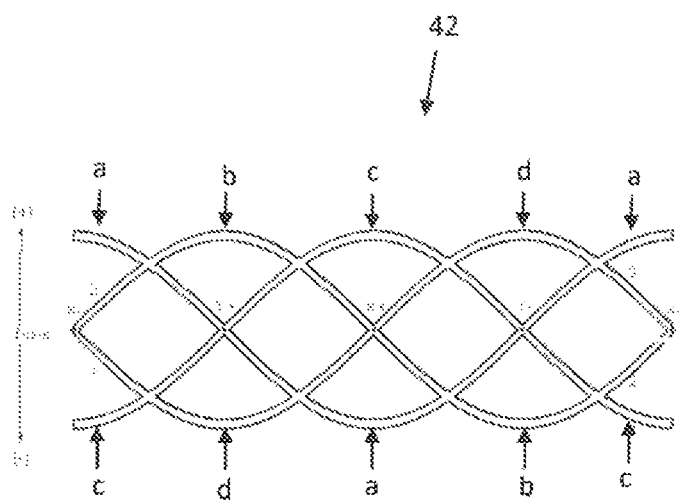

ADVANCED SAFE INFANT MRI SYSTEM COMPRISING MRI COMPATIBLE INFANT WARMING MATTRESS

RELATED APPLICATION DATA

The present application claims priority to U.S. Provisional Application No. 62/561,757, filed on Sep. 22, 2017, which is incorporated herein by reference in its entirety.

TECHNICAL FIELD

The present invention relates generally to a patient-centered infant diagnostic system. More particularly, the invention relates to an infant magnetic resonance imaging (MRI) sub-system incorporating infant warming therapy and advances in MRI quality for effective diagnosis.

BACKGROUND OF THE INVENTION

Roughly 1 in 10 infants are born premature. Early diagnosis of potential injury or disease in premature infants can lead to early intervention which in turn can save lives. Magnetic resonance imaging (MRI) is a safe, non-ionizing radiation-based diagnostic imaging tool that is routinely used in the characterization of illnesses in the first few hours of life.

Newborns that need special care are typically placed in a specialized area, such as an intensive care unit (ICU) or neonatal intensive care unit (NICU) within a hospital. Infants in an ICU/NICU are typically required to stabilize prior to initiating an MRI study, which traditionally involves leaving the ICU/NICU. Stabilization can take days or even weeks, by which time an injury or disease may manifest, and in some cases may become irreversible, leaving very little or no room for clinical intervention.

Additionally, premature babies and term newborn infants that require a special environment are typically kept in an infant warmer or isolette (at temperatures up to 39° C., humidity up to 100% and oxygen up to 100%) and may be coupled to several life sustaining devices and vital sign monitoring equipment for continuous care and monitoring. This makes neonatal transport anywhere outside of the ICU/NICU complicated, since all of the life-sustaining and vital sign monitoring equipment have to accompany the infant. Furthermore, MRI rooms are not designed to be receptive to infants who struggle to maintain normothermia. Instead, conventional MRI rooms are maintained at lower temperatures to prevent a patient's core body temperature from exceeding the FDA limit of 1° C., which although suitable for adults, is not tolerated by pre-term and term infants. Accordingly, sick infants often lose body temperature during transport from the ICU/NICU and during the MRI procedure, which can be deleterious to their health. Integration of an effective infant warming therapy for thermoregulation of infants during transport and MRI procedure is therefore required.

Generally, isolettes are proportionately sized to meet or exceed various performance parameters required by the International Electrotechnical Commission (IEC) standards, such as for example the uniformity of air flow over a patient mattress. A conventional isolette based on forced convection air warming requires the use of motors and specialty electronics. Additionally, conventional stationary and transportable isolettes use high power of roughly 350-500 W and require a power supply of 120 VAC/230 VAC. Furthermore, transportable isolettes are typically made of many parts, making their maintenance cumbersome. Considerable MRI down time is expected between patient use of such isolettes since they have to be cleaned and disinfected after each use, which can take anywhere from 4 hours to a day based on hospital practice. Additional modular MRI incubators or substitute MRI patient tables with integrated incubators and skin temperature monitoring electronics may be used at added cost, however such incubators and associated MRI equipment are not practical for continued clinical use.

Also, larger adult radiofrequency (RF) coils in MRI systems, when used to obtain images from infants, have a very low filling factor (defined as loading volume divided by the coil volume) and are therefore not optimum. This is especially true when the imaging devices are placed around an isolette. When used on infants, not only do adult-sized scanners with adult-sized imaging devices compromise image quality, but they also prolong scanning times, which can be inconvenient for sick infants who often require on-the-spot (i.e., stat) diagnosis.

Additionally, due to their small size, an infant, when scanned on a conventional adult-sized MRI, is immediately subjected to low IEC/FDA limits for whole body heating since their entire body fits inside the body transmit coil. The IEC/FDA limits are known in the art and are generally as follows:

IEC/FDA Limits for Whole Body Heating
Normal mode limit (suitable for all patients)—0.5 degrees C. or 2 W/kg
First level controlled mode (medical supervision)—1.0 degrees C. or 4 W/kg
Second level controlled mode—greater than 1 degree C. or 4 W/kg (requires IRB approval)
IEC/FDA Limits for Localized Heating
Head normal mode limit—38 degrees C. or 3.2 W/kg averaged over head mass
Torso normal mode limit—39 degrees C. or 10 W/kg over any 10 grams
Extremities normal mode limit—40 degrees C. or 10 W/kg over any 10 grams
No first level for head, torso or extremities.

Larger adult body coils, normally tuned for an average adult patient weight (e.g., 170 lbs), experience unloaded conditions with the small infant load (e.g., ≤10 lbs) and therefore expend a majority of their power into the 50Ω termination load. Incident RF power, if not terminated properly, results in a standing-wave which impedes proper measurement and therefore RF transmit chain calibration. At very low RF power, system measurements and specific absorption rate (SAR) algorithms may not be accurate. That is, a system with a 35 kW RF amplifier may have difficulty with calibration at ≤5% of its maximum rating (≤1.75 kW), often leading to ambiguous results and, in some cases, termination of the scan (e.g., when SAR≥100%).

Efforts to reduce peak SAR employing parallel transmit RF coils on commercial scanners has been attempted by driving two conventional linear birdcage designs of the body RF coil separately, using two RF amplifiers with slightly different amplitudes and phases. The birdcage RF coil is well known in the art and includes two end rings connected by several straight segments. In these efforts, there is no change in the body RF coil design (i.e., the entire infant still fits inside the body RF coil volume) with the exception of two drive points as opposed to the conventional analog-quadrature combined single port drive. This alleviates the adult peak SAR problem somewhat, but not entirely, since there may exist non-sinusoidal patterns on the linear drives around the cylinder periphery of the body RF coil. Parallel transmit efforts with surface coils on a cylindrical former give some hope but deviate from the task at hand since more power is needed for generating greater flip angles at volumes away from the RF coil surface (i.e., RF coil center). This is to be expected since there is a considerable field falloff for a surface RF coil from the cylindrical surface inside the central RF coil imaging volume. Additionally, conventional pediatric RF coils used in MRI systems are configured to accommodate 4.5 year old patients weighing 23 kilograms but are not suited for infants weighing anywhere between 450 grams to 4.5 kilograms. There exists a need, therefore, for custom infant sized imaging devices to acquire optimum quality images in a shorter amount of time.

SUMMARY OF THE INVENTION

For at least the abovementioned reasons, there is an unmet need for point of care diagnosis to delineate precisely the onset of injury and determine its pathway, onset, and response to therapy or minimally invasive surgery. The need for a custom warming system and SAR-efficient RF coil design for application to a high signal to noise diagnostic imaging device is now apparent.

According to an aspect of the invention, a pediatric magnetic resonance imaging (MRI) sub-system is provided. The pediatric MRI sub-system includes an isolette including a patient section for accommodating a patient. The subsystem also includes an MRI compatible infant warming mattress arranged within the patient section of the subsystem. The warming mattress includes an interior space and a conduction heating system at least partially arranged in the interior space. The conduction heating system is configured to conduct heat to the interior space of the infant warming mattress.

In an embodiment, the pediatric MRI sub-system also includes a local RF coil array positionable within the patient section of the isolette.

In an embodiment, the conduction heating system includes an MRI transparent host medium arranged in the interior space and having a prescribed specific heat.

In an embodiment, the conduction heating system includes at least one heater operative to heat the host medium via conduction heating.

In an embodiment, the prescribed specific heat of the host medium is between 0.1 and 0.9 cal/g° C.

In another embodiment, the host medium has a thermal conductivity between 0.01 and 0.5 W/m·K.

In another embodiment, the host medium has a specific heat of about 0.23 cal/g° C. (963 J/Kg·K) and a thermal conductivity of about 0.065 W/m·K.

In another embodiment, the at least one heater of the conduction heating system of the infant warming mattress is located remote from the interior space of the infant warming mattress. The conduction heating system further includes at least one pump in fluid communication with the MRI transparent host medium in the interior space. The at least one pump is configured to cycle the MRI transparent host medium through the interior space.

In another embodiment, the at least one heater of the conduction heating system includes a heat insulator operative to prevent direct contact between the infant warming mattress and the at least one heater.

In another embodiment, the conduction heating system includes at least one of an infrared, ultrasonic, microwave RF or optical heating device.

According to another aspect of the invention, a pediatric MRI system is provided. The pediatric MRI system includes a magnet-gradient assembly and a transmit and/or receive body RF coil configured to image a portion of a patient. The pediatric MRI system also includes the pediatric MRI sub-system according to the first aspect of the invention.

In an embodiment, the body RF coil includes four individual circuit loops arranged in a sinusoid pattern over a cylinder surface. Each of the circuit loops are phase shifted from an adjacent circuit loop by 90 degrees.

In another embodiment, the pediatric MRI system further includes circuitry configured to drive two of the four circuit loops 180 degrees out of phase.

In another embodiment, the pediatric MRI system further includes circuitry configured to individually drive each of the four loops.

In another embodiment, the at least one local RF coil comprises a single channel, transmit and/or receive RF coil.

In another embodiment, the at least one local RF coil comprises a multi-channel, receive-only RF coil.

In another embodiment, the magnet-gradient assembly of pediatric MRI system comprises at least one superconducting wire.

In another embodiment, the pediatric MRI system further includes a conduction cooling system for controlling a temperature of the magnet-gradient assembly via heat transfer through the at least one superconducting from the conduction cooling system.

In another embodiment, the conduction cooling system includes a cryogen-free cooler.

In another embodiment, the conduction cooling system further includes a host receptor arranged within the magnet-gradient assembly and housing a cooling medium. The host receptor is cooled by the cryogen-free cooler. The host receptor also has a mass sufficient to maintain system enthalpy over a predetermined time period.

In another embodiment, the host receptor is held in a vacuum to isolate the cooling medium from the ambient temperature.

In another embodiment, the cooling medium includes a primary medium and a secondary medium, each having a specific heat of 50 J/Kg·°K and a total heat capacity between 500-1,000 J/Kg at 10-20K.

The present application relates and refers to the following prior U.S. patents and Provisional Patent Applications, the contents of which are incorporated herein by reference in their entirety:

U.S. Pat. No. 8,147,396, issued on Apr. 3, 2012, titled "Neonate Imaging Sub-system," involving a combination of life sustaining and monitoring equipment and accessories used on a magnetic resonance imaging (MRI) system;

U.S. Pat. No. 6,992,486, issued on Jan. 31, 2006, titled "Radio Frequency Coil For Resonance Imaging Analysis Of Pediatric Patients," involving a pediatric coil for magnetic resonance that can be operatively coupled to an isolette to increase the resolution of a magnetic resonance scan of a neonate inside the isolette;

U.S. patent application Ser. No. 15/560,333, filed on Sep. 21, 2017; titled "Isolette Environment Controller and Method;" and U.S. patent application Ser. No. 15/560,328, filed on Sep. 21, 2017, titled "Safe Infant Imaging system," involving an improved isolette that is patient, operator, and equipment safe and adapts to an environment without compromising the equipment operation or the performance of the isolette, accessory or diagnostic imaging system.

BRIEF DESCRIPTION OF THE DRAWINGS

FIG. 3B is a X-Y cross-sectional view of the magnet-gradient assembly of FIG. 3A.

FIG. 4A is a schematic view of a conventional volume birdcage body RF coil design.

FIG. 4B is a schematic view of the conventional volume birdcage body RF coil design of FIG. 4A, in an open planar configuration.

FIG. 4C is a schematic view of an exemplary body RF coil design in an open planar configuration according to an aspect of the present invention.

DESCRIPTION OF THE INVENTION

As used herein, the term "sub-system" relates generally to a subset of the pediatric MRI system, mainly the pediatric MRI system without the main diagnostic imaging equipment.

Figure 1:
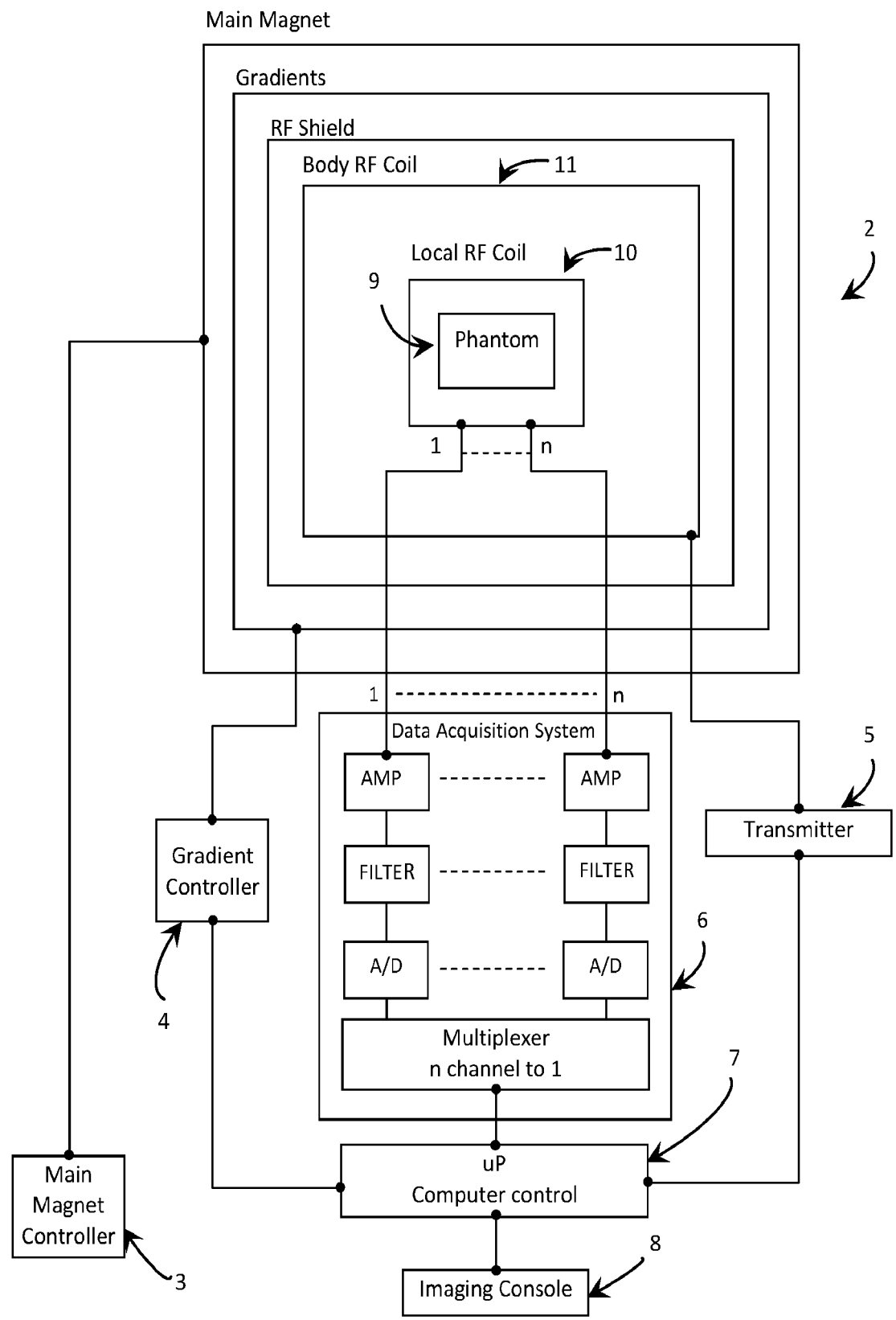
FIG. 1 is a block diagram of a conventional magnetic resonance diagnostic system.

With reference to FIG. 1, a block diagram of a conventional MRI diagnostic system 2 with a magnet, room temperature shims, gradients, RF shield and body RF coil 11 is depicted. The body RF coil 11 defines an imaging volume set up consisting of at least one local RF coil array 10. An imaging phantom 9 is depicted in place of a human subject in the imaging volume of the MRI diagnostic system 2. The MRI diagnostic system 2 includes a main magnet controller 3, a gradient controller 4, a transmitter 5 and a data acquisition system 6, as is conventional. A computer controller 7 controls the operation of the system, and system data is provided to a user through an imaging console 8. The local RF coil array 10 sends and receives MRI data and control signals data to and from the data acquisition system 6.

Conventionally, high field magnets are preferred to obtain high signal to noise ratio (SNR) and therefore high image resolutions on small anatomy. Conventional high field magnet technology employs dual vacuum chambers for the helium and nitrogen gas necessary to maintain the superconductivity of the current carrying wire(s) in the magnet, and therefore the resulting main magnetic field. Slight variation in magnet temperatures, however, can trigger an undesirable quench, and a rapidly quenching magnet may produce unnecessary vibration and excessive noise. Additionally, the sudden release of large amounts of helium during a magnet quench may deprive the patient and healthcare personnel of oxygen. Moreover, these undesirable magnet quenches may result in considerable MRI downtime and are expensive to correct. Furthermore, stronger and faster switching time varying gradients normally kept outside the magnet structure can also cause eddy current artifacts in the MRI image, especially on higher resolution and faster scans.

Accordingly, heating due to vibration, coil resistance and eddy currents may be significant. For example, without considering sinusoidal functions, the resistive heat generated from driving one gradient set with 25 mΩ internal resistance at 150 A is about 563 W. Considering the cumulative effect of multiple axes driven at peak power, this heat generation is significant. Magnet winding coils are conventionally cooled and housed in two vacuum chambers (one for helium and one for nitrogen; not shown) for isolation from the ambient room temperature. Water cooling is conventionally used to reduce the resistive heat generated by the epoxy-potted, fast switching 0.1-10 KHz gradients (typical inductance in the order of 10-50 mH). This, however, requires a dedicated source and means of quickly cycling the heat generated.

Figure 2:
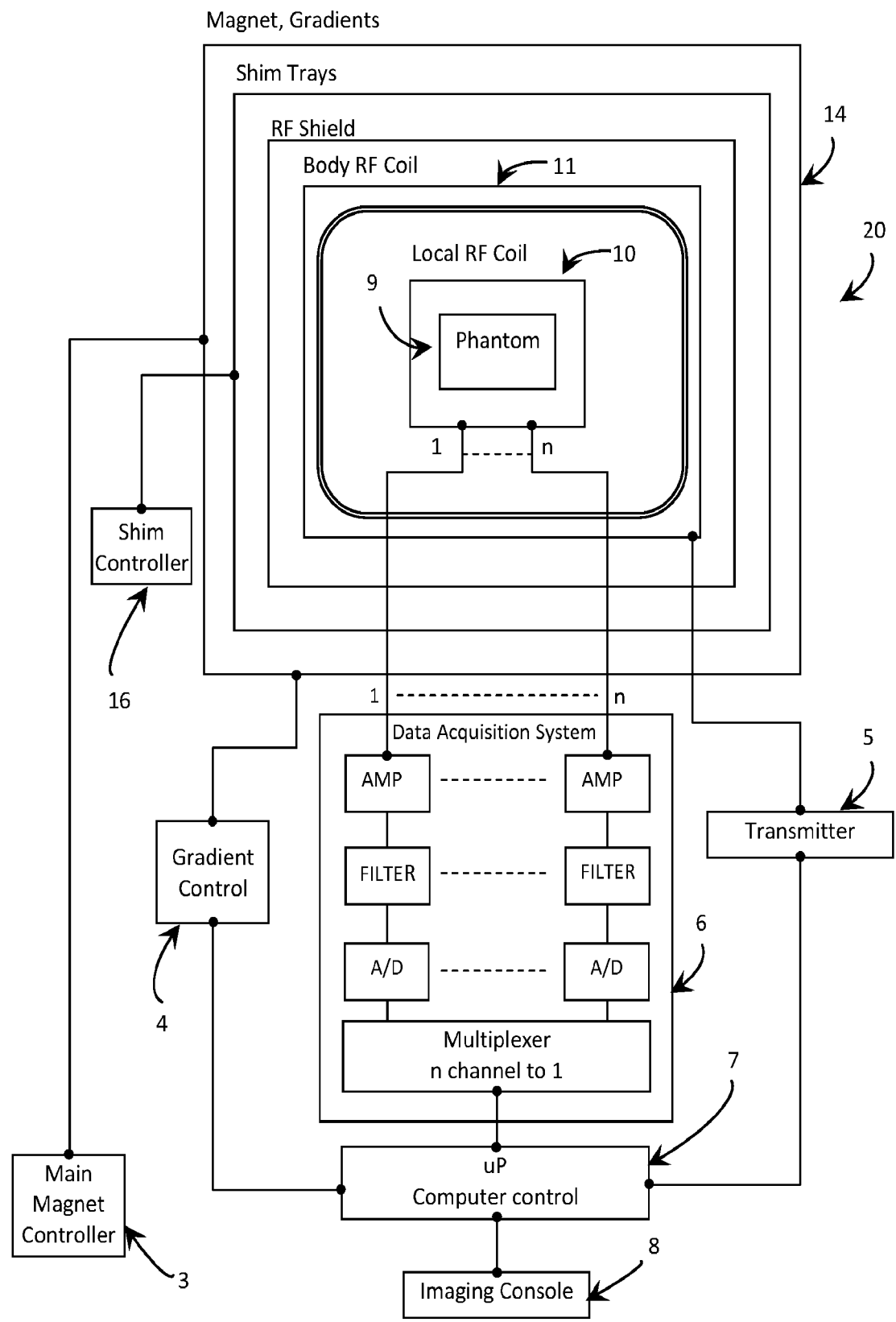
FIG. 2 is a block diagram of an exemplary magnetic resonance diagnostic system according to an aspect of the invention.

With reference to FIG. 2, a block diagram of an MRI diagnostic system 20 according to an aspect of the present invention is depicted. The MRI diagnostic system 20 of the present invention differs from that of FIG. 1 most notably in that it includes an integrated magnet-gradient assembly 14. As used herein, integrated magnet-gradient assembly is defined as a combination of an MRI magnet system and a gradient system. The combination of the MRI magnet system and the gradient system may be either in a common assembly or may include one system merged partially or wholly into the other system. In the embodiment depicted in FIG. 2, the MRI magnet system and the gradient system are merged in to one common assembly. The integration of the magnet and gradient assemblies simplifies the design and enhances system stability and performance with vibration-free, virtually noise-free, passive quenches. Further, the patient-centered MRI diagnostic system 20 of the present invention is in the best interest of the patient, user and hospital as it is custom, light-weight, helium-free, and non-cryogen cooled. The MRI diagnostic system 20 also achieves low fringe field and rapid ramping ability.

As is conventional, the MRI diagnostic system 20 may also include shim assemblies, an RF shield and a body RF coil 11. The body RF coil 11 defines an imaging volume set up including at least one local RF coil array 10. The body RF coil 11 may be a transmit and/or receive RF coil. The local RF coil array 10 may include one or more local RF coils, such as for the brain, heart, spine, wrist, knee, etc., and may come in close contact with the patient for obtaining high signal to noise over the anatomy under investigation. The local RF coil array 10 may also be a transmit and/or receive coil array. For example, the local RF coil array 10 may include one or more single channel, transmit and/or receive RF coils. In another example, the local RF coil array 10 may include one or more multi-channel, receive-only RF coils. An imaging phantom 9 is depicted in place of a human subject in the imaging volume of the MRI diagnostic system 2. The MRI diagnostic system 20 includes a main magnet controller 3, a gradient controller 4, a transmitter 5 and a data acquisition system 6, as in the conventional MRI diagnostic system 2 of FIG. 1. A computer controller 7 controls the operation of the system, and system data is provided to a user through an imaging console 8. The local RF coil array 10 sends and receives MRI data and control signals data to and from the data acquisition system 6. The presence of shim assemblies (e.g., passive and active) and a shim controller 16 allows homogenization of the main magnet field (making it uniform) over the anatomy of investigation, suitable for high resolution MR imaging and spectroscopy.

Figure 3A:
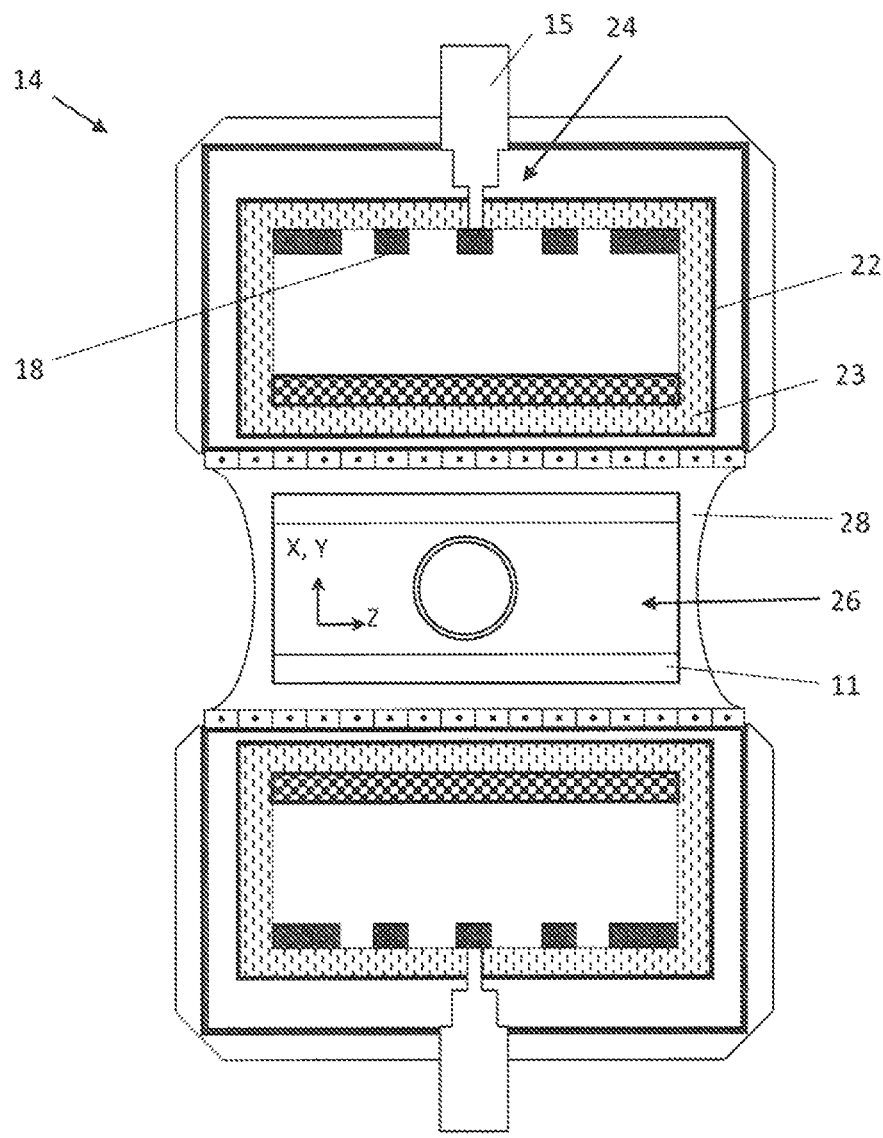
FIG. 3A is a cross-sectional view of the magnet-gradient assembly of the magnetic resonance diagnostic system of FIG. 2.
Figure 3A:
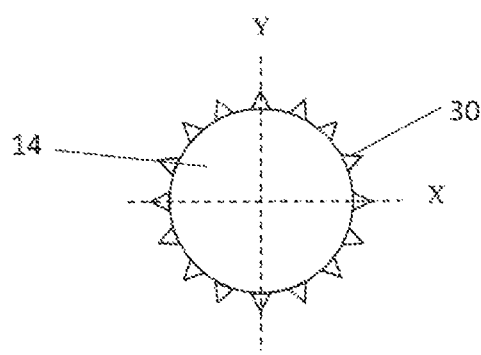
Figure 5A:
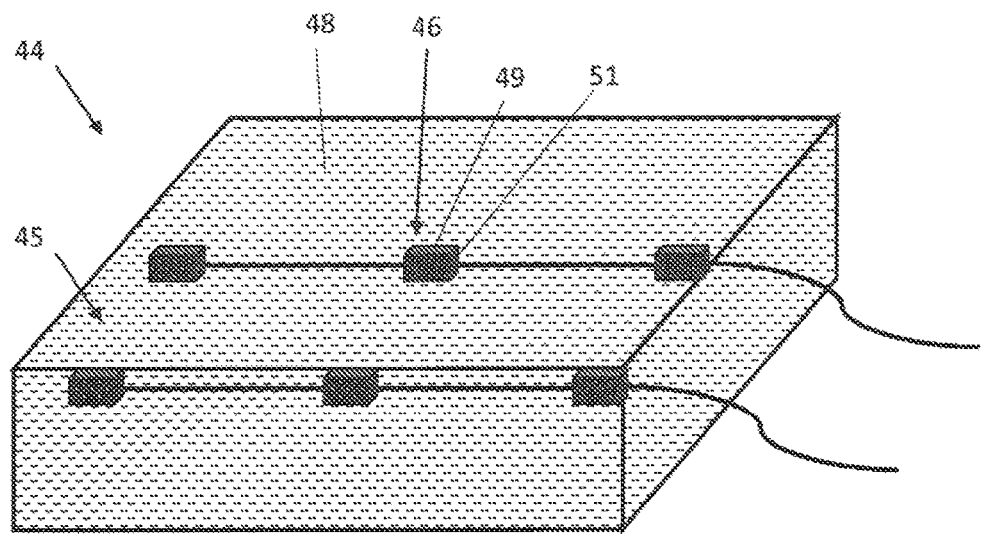
FIG. 5A is a schematic diagram of an exemplary infant warming mattress according to an aspect of the invention.
Figures 5B, 5C, 5D, 5E:
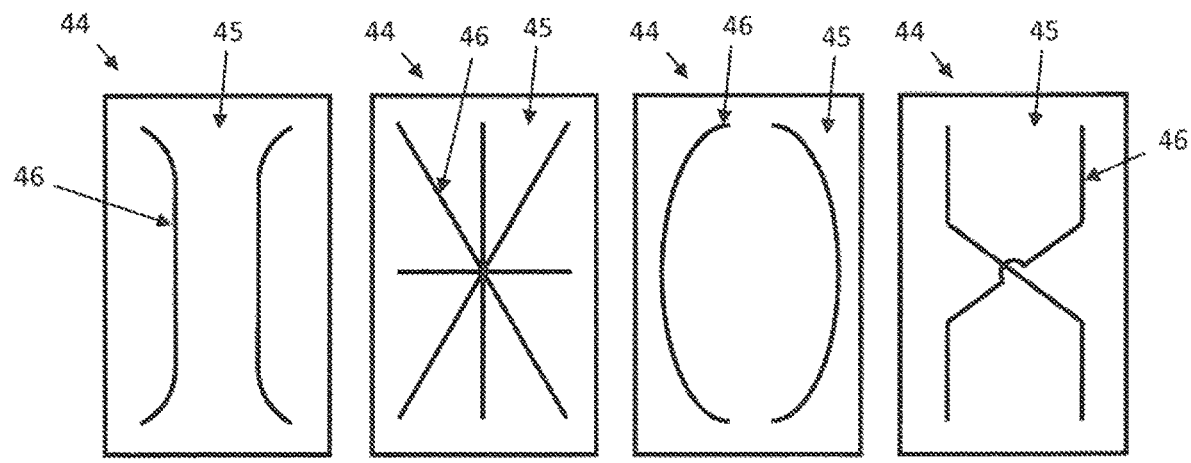
FIG. 5B-E are schematic diagrams of various embodiments of infant warming schemes for the infant warming mattress of FIG. 5A.

With reference to FIG. 3A, a cross-sectional view of the integrated, light-weight, helium-free and non-cryogen cooled magnet-gradient assembly 14 of the pediatric MRI system 20 of FIG. 2 is depicted. By reducing the metal in the inner chamber where the gradients and magnet coils reside, considerable eddy currents may be eliminated.

The magnet-gradient assembly 14 of the MRI system 20 includes a conduction cooling system 24 for quickly detecting and resolving temperature rise in the magnet-gradient assembly 14, such as for example, by controlling a temperature of the magnet-gradient assembly 14 via heat transfer through at least one superconducting wire 18 from the conduction cooling system 24. The magnet-gradient assembly 14 includes magnet coils of the at least one superconducting wire 18, made of materials with high thermal conductivity to serve as a conduit for heat transfer (conduction cooling) to the magnet-gradient assembly 14 from the conduction cooling system 24. Use of copper, niobium-titanium or high temperature wire (for example, copper 400 W/m·K) with high current carrying density of 600 A/mm$^2$, for example, may be used. The magnet-gradient assembly 14 of the present invention achieves <½ the weight of prior art magnet assemblies and, due to enhanced magnet operation, achieves at least three times the field strength, making it highly suitable for enhanced diagnosis in a shorter exam time.

In an embodiment, the conduction cooling system 24 may include a cryogen-free cooler 15. In a further embodiment, the conduction cooling system 24 may also include a host receptor 22 arranged within the magnet-gradient assembly 14 and cooled by the cryogen-free cooler 15. As used herein, a host receptor 22 is defined as an enclosure that houses the magnet and gradient systems in the magnet-gradient assembly 14 as well as a cooling medium 23. The temperature of the superconducting wire 18 necessary to sustain the main magnetic field is held steady by a cooling medium 23 in the host receptor 22. The cooling medium 23 in the host receptor 22, therefore, may have very low specific heat, for example, ranging from 0.005 to 0.05 J/g·K. In an embodiment, the cooling medium 23 in the host receptor 22 may have a specific heat of, for example, 0.02 J/g·K. The host receptor 22 may be held in a vacuum to substantially isolate the cooling medium 23 of the host receptor 22 and temperature of the magnet and gradient systems (4-30K) from the ambient room temperature of 25° C. One or more cooling mediums 23 with different heat capacities may be used in combination within the host receptor 22.

The mass of the host receptor 22 may be capable of maintaining system enthalpy over a predetermined time period (i.e., to provide high latency to sustain main magnet temperature and the resulting magnetic field during a brief interruption or power disturbances). That is the host receptor 22 may have substantial mass to ensure steady state superconducting wire 18 temperature in the safe operating zone (below critical [maximum] temperature cutoff $T_c$ for a superconducting wire 18) necessary to maintain a stable magnetic field. Infant size magnet-gradient assemblies, however, occupying roughly half to a third of the adult scanner volume can require lower heat capacity in the order of 500-1,000 KJ/Kg.

According to an aspect of the invention, therefore, a high enthalpy host receptor 22 housing a cooling medium 23 of liquid nitrogen is provided in the magnet-gradient assembly 14. The host receptor 22 may operate anywhere between 4-99° K and may be covered with a 0.001-0.060" thick metal. The host receptor 22 may be conduction cooled with a 1-4 W cryogen-free cooler 24 and held in vacuum to isolate it from the ambient room temperature. The cooling medium 23 may include primary and secondary cooling mediums 23 with a specific heat of ≥50 J/Kg·° K and a total heat capacity anywhere between 500-1,000 J/Kg at 10-20K. The host receptor 22 is sufficient to support the magnet-gradient assembly 14 coil operation, resulting in a stable magnet and gradient field over an imaging volume 26. The mass of the host assembly 22 can provide sufficient inertia to enable field switching or ramping to higher field strength up to a prescribed limit or de-ramping to a lower magnetic field for enhanced safety or other purposes without affecting magnet integrity or propagating a magnet quench.

A passive shim liner with a plurality of symmetric trays and a plurality of small pieces of steel distributed along each tray length from front to the back of the magnet-gradient assembly 14 inside the main magnet bore is intended to homogenize the main magnetic field over the imaging volume 26. Conventional circular and elliptical cross-section magnets maintain two-axes symmetry (i.e. in four quadrants), and are therefore preferred to have a total number of trays divisible by 4. Accordingly, the magnet gradient assembly 14 according to the present invention may have 32, 48, 64, etc. . . . trays and a number of small pieces of steel within each tray ranging from 16-128 pieces, depending on the level of control needed to homogenize the main magnet field along the magnet-gradient assembly axis (Z). One or more shim trays 28 can be used, or a single tray 28 can be further sub-divided to homogenize field strength at one or more field strengths (e.g., 3 T and 1.5 T). With reference to FIG. 3B, small pieces of steel 30 may be lined outside the magnet-gradient assembly 14 (<10% of the main magnet weight) to capture the flux extending out of the magnet-gradient assembly 14 volume to return the flux back to the magnet-gradient assembly 14. This is done to preserve the system magnetic flux or magnetic field energy without significantly diminishing the magnetic field strength over the imaging volume 26 while exhibiting minimum interaction with neighboring equipment.

The magnet-gradient assembly 14 inner bore diameter (excluding the body RF coil 11 and RF shield) may be 30-50 cm and the magnet-gradient assembly 14 outer diameter may be 80-140 cm. The magnet-gradient assembly 14 may operate between 1.5 T-4 T. The gradient design may be either the "thumb print" minimum inductance as taught by Turner et al. (Turner, R. Comparison of minimum inductance and minimum power gradient coil design strategies. In: Book of abstracts: Eleventh Annual Meeting of the Society of Magnetic Resonance in Medicine. Berkeley, Calif.: ISMRM, 1992: 4031) or others. First order shimming of the main magnet field is possible by superimposing small fields on the X, Y and Z gradient coils to further homogenize the main magnet field over the imaging field of view (FOV). The overall weight of the magnet-gradient assembly 14 may be 600-1,000 Kgs, distributed over a 3'×5' floor footprint. Accordingly, the MR diagnostic system 20 of the present invention simplifies the cooled magnet-gradient assembly 14 into one light-weight structure capable of rapid ramping and safe operation in one or more field strengths, in a stable manner.

Turning to FIGS. 4A-B, a conventional volume birdcage body RF coil design 40 used in, for example, the conventional MRI diagnostic system 2 of FIG. 1 as the body RF coil 11 without the RF shield, is depicted in its actual form in FIG. 4A and in an open planar configuration in FIG. 4B. The conventional volume birdcage body RF coil design 40 provides homogeneous $B_1$ distribution inside the coil volume due to a sinusoidal current distribution in the azimuthal rungs oriented along the cylinder axis (Z). In the open planar configuration with the end-rings broken, the birdcage exhibits a one-dimensional ladder structure.

With reference to FIG. 4C, a four channel, parallel transmit and/or receive sinusoidal body RF coil design 42 used in, for example, the body RF coil 11 in the MRI diagnostic system 20 according to an aspect of the present invention is depicted in an open planar configuration. The body RF coil 11 of the MRI diagnostic system 20, may therefore be of a single structure. As seen the open planar configuration, the sinusoidal body RF coil design 42 of the present invention exhibits sinusoid patterns for four individual circuit loops that are phase shifted by 90° from each other on a cylinder surface. For example, as depicted in FIG. 4C, loop b is shifted 90° from loop a, loop c is shifted 90° from loop b, loop d is shifted 90° from loop c, and loop a is shifted 90° from loop d. Such sinusoidal pattern on the cylinder surface results in homogeneous $B_1$ field distribution in the coil volume.

In an embodiment, the MRI diagnostic system 20 incorporating the body RF coil design 42 for the body RF coil 11 may include circuitry configured to drive two of the four circuit loops of body RF coil design 42 180° out of phase. For example, as depicted in FIG. 4C, loops a and c may be driven 180° out-of-phase to create a linear mode similar to that in the conventional volume birdcage body RF coil design 40. Likewise, the a-c and b-d loop pairs may be combined with the use of a standard Wilkinson quadrature combiner to create and drive a single circularly polarized mode, similar to that used in the conventional volume birdcage body RF coil design 40.

In an alternative embodiment, the MRI diagnostic system 20 may include circuitry configured to individually drive each of the four loops. For example, each loop of the sinusoidal body RF coil design 42 of FIG. 4C may be driven individually with four transmit channels, unlike the conventional volume birdcage body coil design 40, which is limited to two transmit channels. The whole body transmit body RF coil design 42, which is preferably driven with one or more independent RF transmitters for a total power of roughly 8 kW at 3 T (128 MHz) may also include an RF shield of microns thick. The use of four independent 2 kW transmitters with amplitude phase control may also be used. Accordingly, the sinusoidal body RF coil design 42 of the present invention offers a high level of uniformity, comparable to the conventional volume birdcage body RF coil design 40 depicted in FIGS. 4A-B. The sinusoidal body RF coil design 42 of the present invention, therefore, may be advantageous over surface coil parallel transmit designs that focus on contiguous volumes. The sinusoidal body RF coil design 42 of the present invention offers additional degrees of freedom in optimizing RF power deposition and lower local SAR because all 4 loops focus over the common central imaging volume.

In an embodiment, the sinusoidal body RF coil design 42 of the present invention may be lined with high permittivity material (e.g., $\varepsilon_r$ of 200-5,000) and low conductivity (e.g., $\sigma \leq 0.05$ S/m) to confine the RF transmit field to the imaging FOV and adjust the RF termination on the shield. Higher value permittivity materials may be of use and are available at elevated costs. Higher conductivity materials or solutions can be used, but their effect may reflect in lower coil loaded Q's since they will present additional loading to the RF coils, especially at higher frequencies. Accordingly, appropriate permittivity and conductivity may be chosen based on the operating frequency and the imaging application. Transmit RF field confinement and improved RF homogeneity can be realized with reduced peak and average SARs over the imaging volume, which are highly desirable for infants.

With the sinusoidal body RF coil design 42 of the present invention, the need for oversampling from neighboring anatomy is obviated, thus reducing scan time. Additionally, the use of saturation pulses on areas next to the imaging field of view is obviated, thereby reducing RF power for the MR experiment. Focusing the RF transmit field to a confined volume within the body coil with little or no radiation to volumes outside the body coil effectively shortens the body RF coil design 42 electrical length, and in turn improves performance with better transmit and receive efficiencies over the imaging volume. This feature may also allow physically shortening of the whole-body coil, again improving overall efficiency with subsequent use of a smaller RF amplifier (e.g., 4-6 KW instead of 8 KW amplifier at 3 T [128 MHz]). The reduction of transmit power depends on the effect a given high permittivity material has on body RF coil efficiency based on the anatomy of interest, application and field strength. Since radiative, resistive and patient losses increase with increasing field strength and frequency, the effect of high dielectric materials is expected to be greater at higher operating frequencies. Parallel imaging compatible array coils further enhance image quality. Parallel transmit capability can lead to reduction of peak and average SARs over infants. The sinusoidal RF coil 42 of the present invention may be lined with an acoustic dampening material (e.g., closed cell polyethylene with 1 lb foam density) intended to reduce the audio noises to for example <70 dBA, so the infant is left undisturbed.

Turning now to FIGS. 5A-6B, various embodiments of an infant warming mattress 44 comprising an interior space 45 are depicted. The infant warming mattress 44 may also include a conduction heating system 46 at least partially arranged in the at interior space. As used herein, conduction heating or conductive heating is defined as the transfer of heat between objects via physical contact. The conduction heating system 46 is configured to conduct heat to the interior space 45 of the mattress 44. Heat transfer can be accomplished by solid, liquid and/or gaseous mediums. For example, the conduction heating system 46 may include an MRI transparent host medium 48 arranged in the interior space 45 and at least one low power heater 49 for heating the host medium 48 via conduction heating. In an embodiment, the MRI transparent host medium 48 may be a liquid medium. As used herein, MRI transparent is defined as materials that do not possess magnetic resonance properties, (i.e., do not have water protons and therefore do not exhibit MR signals that can show up as artifacts in the MR image which can interfere with a clinical diagnosis). The host medium 48 may therefore have a prescribed specific heat in order to keep the infant warming mattress 44 warm. Conventional infant warming methods require one-hour prewarming of the incubators. The infant warming mattress 44 of the present invention, however, incorporates conduction heating (similar to conduction cooling discussed above for cooling the MRI magnet-gradient assembly 14) with <50 W total power to arrive within ±1° C. of the set temperature from baseline in 10-15 minutes, and with roughly 8-20 W (typically 14 W) once the set temperature is reached to maintain steady-state. Accordingly, the incorporation of the infant warming mattress 44 of the present invention may provide an effective warming therapy to support infant life and permit immediate point of care diagnostic ability for sick infants, which may in turn lead to prompt clinical interventions to save lives.

In an embodiment, the warming mattress 44 (weighing <4.5 Kg (<10 lbs)) may be configured to reach a specified temperature range anywhere between 30-40° C. within 10-15 minutes with a proper choice of low watt heater 49 configurations and a host medium 48 with proper specific heat and thermal conductivity. A host medium 48 with a high specific heat will react very slowly to the heat supplied and a host medium 48 with a low specific heat, with the small mass employed here, will raise the temperature of the mattress very quickly. The host medium 48 may therefore be chosen to have a specific heat between 0.1 and 0.9 cal/g° C., while feedback sensors, control algorithms and heating mechanisms controlled by a micro-computer may be employed to arrive at the set temperature quickly and maintain steady state. The host medium 48 may also be chosen to have a thermal conductivity between 0.01 and 0.5 W/m·K. In an embodiment, the host medium 48 may have a specific heat of about 0.23 cal/g° C. (963 J/Kg·K) and a thermal conductivity of about 0.065 W/m·K. As used herein, thermal conductivity is defined as the rate at which heat is transferred by conduction through a unit cross-section area of a material, when a temperature gradient exists perpendicular to the area.

With such low power demands the infant warming mattress 44 can be powered by 24 VDC source for example, by two 12 V automotive batteries in series. To illustrate the power efficiency of the system, the two 12 V, 38 AH batteries operating in series can support 60 hours of continuous operation, which is adequate for the MRI procedure and widespread use of the infant warming mattress 44 in support of ambulance and air transport operations. For practical MRI uses, a 20 AH battery capacity may be sufficient. Changes in ambient room temperatures have very little effect on the operation of the infant warming mattress 44, which may be disposed inside a plastic enclosure to provide isolation from the ambient surroundings.

FIGS. 5B-5E illustrate various conduction heating system 46 patterns in which the heaters 49 may be disposed within the mattress 44. It is to be understood that there may be additional patterns that can be used which satisfy MRI constraints, such as not forming closed loops, and are intended to preserve overall scanner performance, including image quality.

Figure 6A:
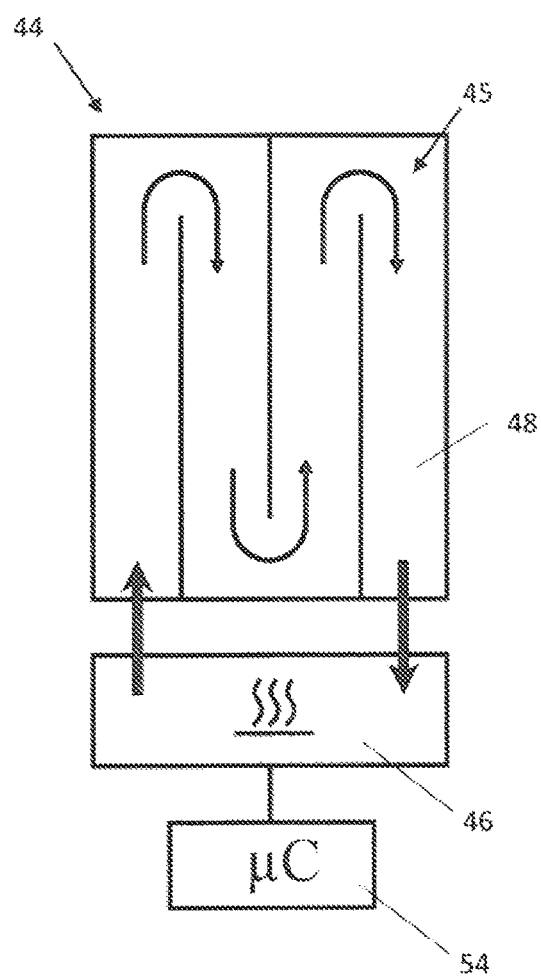
FIG. 6A-B are schematic diagrams of various alternate embodiments of infant warming schemes for the infant warming mattress of FIG. 5A.
Figure 6B:
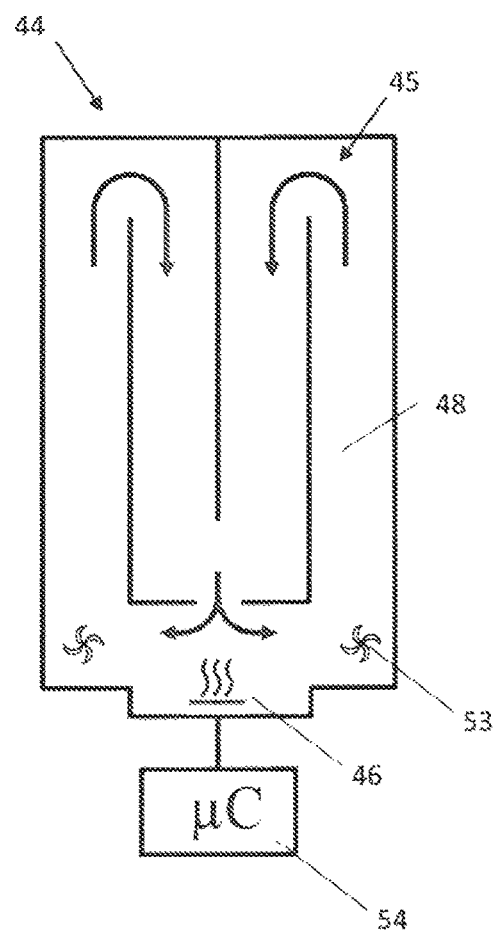

FIGS. 6A-B depict embodiments of an infant warming mattress 44 in which microcontrollers 54 cycle pre-warmed host medium 48 for even heating. The at least one heater 49 (not shown in FIG. 6A or 6B) may be located remote from the interior space 45 of the mattress 44, in a common non-imaging area of the MRI diagnostic system 20, and the conduction heating system 46 may further include at least one motor and/or at least one pump 53 (depicted in FIG. 6B) in fluid communication with the host medium 48. The designs of FIGS. 6A and 6B require additional power necessary to run the motor and/or pump 53, but the heaters 46 remain clear of the imaging volume, unlike the first embodiment described with reference to FIG. 5.

Direct heating is avoided in both embodiments to prevent overheating of the mattress 44 surface and the RF coil. For example, heat insulators 51, depicted in FIG. 5A, may be employed in the areas where the heaters 49 are provided to prevent direct contact of the heaters 49 with the mattress 44 surface and with the coil surface. In addition, little or no heating is possible by RF alone in either embodiment. The infant warming mattress 44 may be isolated from the surrounding environment and the electronics may be isolated from the coil and isolette or infant warming enclosure, which can experience high temperatures, high humidity levels and greater oxygen content.

The infant warming mattress 44, according to either embodiment, imposes fewer constraints when used in combination with RF coils. Thermal fuses and fuses that open with high current and/or when temperatures exceed allowable ranges may be implemented. High permittivity material with very little or no conductivity can be used in or near the local array coil, or in or near the infant warming mattress 44 and the patient to reduce SAR and increase SNR of the MRI exam. Although two embodiments of the infant warming mattress 44 are described herein, it is to be understood that their combination, including any other means such as, infrared, ultrasound, microwave RF, optical etc. . . . to warm the infant warming mattress 44 may be implemented.

Figure 7:
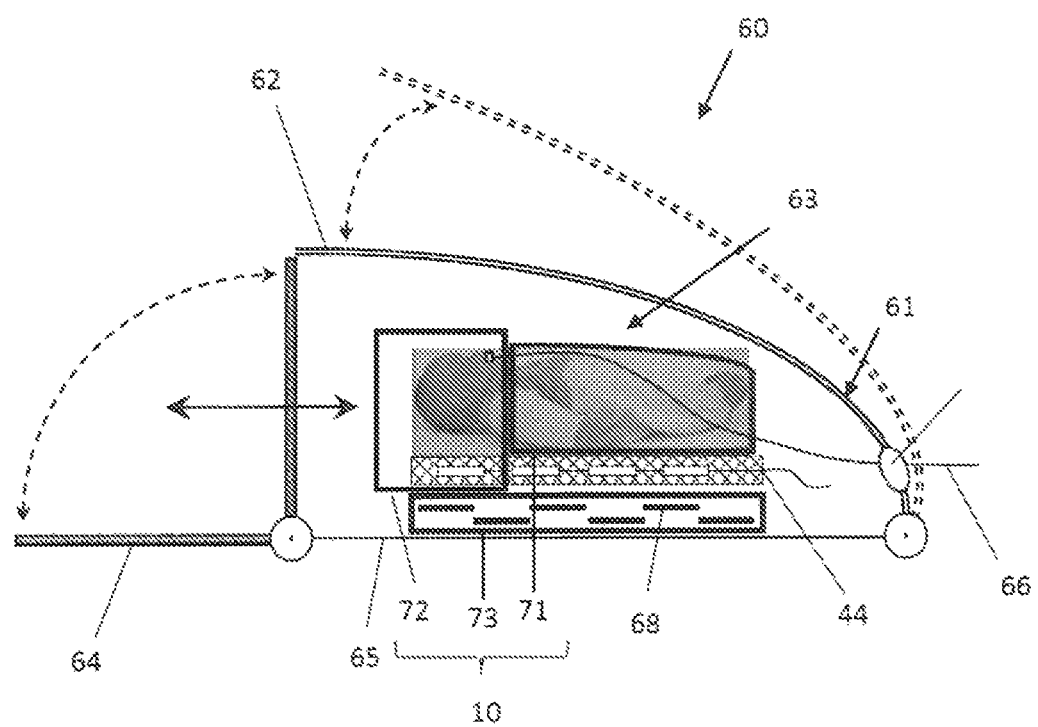
FIG. 7 is a schematic diagram of an exemplary infant magnetic resonance imaging (MRI) sub-system according to an aspect of the present invention.

With reference to FIG. 7, a pediatric MRI sub-system 60, including an isolette or infant warmer 61, a local RF coil array 10 and the above-described infant warming mattress 44, may be employed in the MRI diagnostic system 20. Fresh air at a minimum rate of 1 Liter per minute may be supplied to the pediatric MRI sub-system to maintain carbon dioxide levels to below OSHA safety levels of 3% (30,000 ppm). Fresh air supply may be from medical air tanks during transport. Fresh air supply may also be from available hospital wall outlets throughout the complex, especially in the pediatric and MRI sections or inside the MRI scan room during the MRI exam.

The local RF coil array 10 of the present invention is positionable within the patient section of the infant warmer and is therefore configured to withstand exposure to relatively higher temperatures (up to 39° C.), high levels of humidity (of up to 100% rH) and greater levels of oxygen (up to 100%) that are typical of isolettes or infant warmers. The pediatric MRI sub-system 60 of the present invention may simplify the patient set-up process in order to provide complete emergency access, and can provide a safe warming therapy system for infants without compromising MRI performance. The pediatric MRI sub-system 60 may also provide high SNR imaging devices capable of safe operation in the presence of the warming therapy to aid diagnosis. The pediatric MRI sub-system 60 also can provide a highly-efficient MRI system capable of safe operation in the presence of the warming therapy and associated patient care, life sustaining and vital signs monitoring equipment to aid diagnosis. Accordingly, the pediatric MRI sub-system 60 incorporated with the MRI diagnostic system 20 of the present invention offers a compact, light-weight, cryogen-free MRI system with high performance magnet, gradient and RF coils that can be placed in any clinical hospital section with minimal restrictions.

The infant warmer 61 includes a patient section 63 designed to accommodate up to $98^{th}$ percentile infants and three-month-old patients with a total body weight up to 4.5 Kg and an overall length of 55 cm. The infant warmer 61 is positionable relative to the magnet-gradient assembly 14 of the MRI system 20. The local RF coil array 10 may include one or more local RF coils, such as an anterior cardiac/torso array 71, a head array 72 and/or a spine array 73 to provide high signal to noise coverage over the patient. The one or more local RF coils may be single channel, transmit and/or receive RF coils or may be multi-channel, receive-only RF coils. The anterior, cardiac/torso RF coil array 71 may connect to spine array 73 of the patient table and allow cables to flow underneath the patient table to a system receiver. The infant warmer 61 may include an ergonomically shaped anterior dome section 62 with an adjustable and removable cover. In an embodiment, the anterior dome section 62 may include a port for patient life-sustaining and monitoring lines as well as warmer conduits (collectively, 66) for the infant warming mattress 44. In an alternate embodiment, however, separate warmer/RF coil and patient ports may be used. The infant warmer 61 may also include a removable head section 64 with an adjustable rear door with coil ports (not shown) and a table integrated spine section 65. In an alternative embodiment, an integrated head/spine section may be used.

The infant warming mattress 44 and the local RF coil array 10, is positionable within the patient section 63 of the infant warmer 61. Within the infant warmer 61, neighboring (lateral [L-R or cyclic], superior-inferior [H-F]) and diagonal RF coil array (X-Y, Y-Z, Z-X) elements 68 are lapped to minimize their mutual inductance and to reduce cross-talk, thereby increasing combined SNR. RF coil array element 68 sizes are appropriately chosen to cover the brain, spine, heart, abdomen, and extremities in the 98th percentile newborn population and/or infants up to 3 months. Each array element 68 is interfaced to an individual preamplifier to boost SNR as SNR of the entire chain is dependent on the first stage of the receiver. Outputs from the preamplifiers of the array sections (i.e., head, spine, anterior cardiac/torso, etc. . . . ) are routed through a RF shield to the system receiver. To break the circulating RF currents in this RF shield and to minimize the interaction of the cable with the patient, several RF transformers (or baluns or cable traps) may be introduced at equal to or less than quarter wavelength distance at the NMR frequency to isolate adjacent sections of the cables between transformers. This drastically reduces the interaction of the cable to the patient and helps prevent RF burns generally caused due to close proximity of the cable to the patient at high incident RF during a MRI scan.

During MRI operation, receive signals are digitized either on the local RF coil array 10 or remote from the magnet prior to signal combination. Analog, digital, optical or other means may be employed in the receiver chain. Processing and post-processing can be hosted on the imaging console or on separate consoles. MRI scanner electronics can be placed in a 4'×6' area, whereas the imaging operator console can be placed in a 3'×5' area close to the main magnet. Thus, the space required for the pediatric sized MRI is well within 15'×15'. Use of the cryogen-free superconducting integrated magnet-gradient assembly 14 according to an aspect of the present invention as previously described, is preferred to reduce weight, overall size including siting considerations. Integrated RF shield-body RF coil with parallel imaging options for the inventive body RF coil 42 of FIG. 4C is intended to optimize the RF power expended in a MR experiment and thus reduce peak and local SAR. Other array designs and arrangements are possible by one skilled in the art.

The process of a single-step patient transfer on to the warmer on the MRI table is achieved. Immediate patient access is possible by simply tilting the warmer outer cover and removing the coil sections, without adding warmer constraints. Resuscitation is possible on the warmer mattress without removing the patient from the life sustaining and vital signs monitoring equipment.

Narrow and broad band filtering schemes over the NMR spectrum, shielded coaxial cables, better grounding, etc. . . . and double faults are included to reduce EMI/EMC radiation (per IEC 60601-1-2), eliminate undesired harmonics, minimize risks of high voltage exposure while maintaining leakage currents below the required IEC guidelines for medical equipment for safe operation (IEC 60601-1).

A mobile MRI patient table gantry (not shown) may be designed with adjustable restrain mechanisms to accommodate different size oxygen/air tanks and hold them in place during transport, also accommodate monitoring equipment, infusion pumps, injectors and the like with an easy on/off mechanism (not shown).

All of the MRI compatible equipment and accessories (ventilator, monitor, infusion pump, IV bag, oxygen/air tanks, pressure reducers, flow tubes, etc. . . . ) are held on to the mobile MRI patient table and safe to enter the MRI exam suite, whereas non-magnetic and MR unsafe accessory are removed from the mobile MRI table. In the best interest of saving the gases remaining in the MR conditional tanks, quick connect-disconnects are provided to switch over between the gas tanks and central hospital gas supply in a matter of seconds.

Local RF coil-warmer relation remains unchanged in the presence of the MRI system. Imaging devices are positioned without disturbing the patient. Other coil combinations, such as a knee coil, head only coil, wrist coil, abdomen coil, etc. . . . can be realized for use with the MRI scanner and the isolette or infant warmer. Operating the magnet in one or more field strengths can be beneficial to performing suited experiments at the respective field strengths (i.e., brain MRI at higher field strength and hyper-polarized xenon or helium lung MRI at the lower field strengths). Alternatively leaving the magnet at low field after clinical or research use may be beneficial to enhance safety or to allow cleaning personnel or to conserve power. Modifications to the magnet, gradients, shims, RF shield, MRI, transmit chain originating from the transmit body coil, receive chain originating from the local imaging devices, direct or indirect warming systems, support equipment and accessory are plausible after reading this application.

Advantages of the device in accordance with the present invention include that effective warming care can be provided without interference to diagnostic imaging. Further, optimum diagnosis with enhanced SNR without interference to the patient centered warming therapy are provided, as well as a safe magnetic resonance imaging system suited to minimize hazards otherwise leading to unfavorable events (e.g., due to the introduction of hospital equipment and accessory very close to the resonance magnet).

Additional advantages of device in accordance with the present invention include that a warmer, imaging device, diagnostic imaging system combination is provided that is suitable to receive any mild, moderate or severely ill pediatric patient. The device in accordance with the present invention is safe to use and provides very high SNR fit for diagnosis, an efficient SAR RF transmission, optimum reception of MR signals, a MRI compatible infant warming therapy and a small footprint diagnostic imaging system suitable to receive infants and provide optimum care and diagnostics.

The device in accordance with the present invention permits full body infant imaging without restrictions to the warmer, diagnostic imaging equipment, patient care equipment and accessory, and is capable of providing uncompromising clinical care as a result of evidence based diagnosis or prognosis at or the near the onset of infant illness.

The infant specific technology described herein may be readily applied to human and non-human uses. Although the invention has been shown and described with respect to certain preferred embodiments, it is understood that equivalents and modifications will occur to others skilled in the art upon the reading and understanding of the specification. The present invention includes all such equivalents and modifications.

The invention claimed is:

1. A pediatric magnetic resonance imaging (MRI) sub-system, comprising:
   an isolette including a patient section for accommodating a patient,
   an RF coil array positionable within the patient section,
   an MRI compatible infant warming mattress arranged within the patient section, the MRI compatible infant warming mattress comprising:
   an interior space; and
   a conduction heating system at least partially arranged in the interior space and configured to conduct heat to the interior space,
   wherein at least a portion of the conduction heating system is arranged within an imaging volume of the RF coil array.

2. The pediatric MRI sub-system according to claim 1, wherein the conduction heating system comprises an MRI transparent host medium arranged in the interior space and having a prescribed specific heat.

3. The pediatric MRI sub-system according to claim 2, wherein the conduction heating system further comprises at least one heater operative to heat the MRI transparent host medium via conduction heating.

4. The pediatric MRI sub-system according to claim 3, wherein the at least one heater of the conduction heating system is located remote from the interior space of the infant warming mattress, the conduction heating system further comprising at least one pump in fluid communication with the MRI transparent host medium, the at least one pump configured to cycle the MRI transparent host medium through the interior space.

5. The pediatric MRI sub-system according to claim 3, wherein the at least one heater of the conduction heating system includes a heat insulator operative to prevent direct contact between the infant warming mattress and the at least one heater.

6. The pediatric MRI sub-system according to claim 2, wherein the prescribed specific heat of the MRI transparent host medium is between 0.1 and 0.9 cal/g° C.

7. The pediatric MRI sub-system according to claim 2, wherein the MRI transparent host medium has a thermal conductivity between 0.01 and 0.5 W/m·K.

8. The pediatric MRI sub-system according to claim 2, wherein the MRI transparent host medium has a specific heat of about 0.23 cal/g° C. (963 J/Kg·K) and a thermal conductivity of about 0.065 W/m·K.

9. The pediatric MRI sub-system according to claim 1, wherein the conduction heating system comprises at least one of an infrared, ultrasonic, microwave RF or optical heating device.

10. A pediatric magnetic resonance imaging (MRI) system, comprising:
    a magnet-gradient assembly; and
    the pediatric MRI sub-system of claim 1.

11. The MRI system according to claim 10, wherein the local RF coil array comprises one or more single channel, transmit and/or receive RF coils.

12. The MRI system according to claim 10, wherein the local RF coil array comprises one or more multi-channel, receive-only RF coils.

13. The MRI system according to claim 10, wherein the magnet-gradient assembly of the MM system comprises at least one superconducting wire.

14. The MRI system according to claim 13, further comprising a conduction cooling system for controlling a temperature of the magnet-gradient assembly via heat transfer through the at least one superconducting wire from the conduction cooling system.

15. The MRI system according to claim 14, wherein the conduction cooling system comprises a cryogen-free cooler.

16. The pediatric MRI sub-system according to claim 1, wherein the conduction heating system is an active heating system.

17. The pediatric MRI sub-system according to claim 1, wherein the conduction heating system is an electrically-powered heating system.

18. A pediatric magnetic resonance imaging MRI system, comprising:
    a magnet-gradient assembly;
    a transmit and/or receive body RF coil configured to image a portion of a patient
    a pediatric magnetic resonance imagining (MRI) sub-system, comprising:
    an isolette including a patient section for accommodating a patient,
    an MRI compatible infant warming mattress arranged within the patient section,
    the MRI compatible infant warming mattress comprising:
    an interior space; and
    a conduction heating system at least partially arranged in the interior space and configured to conduct heat to the interior space,
    wherein the body RF coil comprises four individual circuit loops arranged in a sinusoid pattern over a cylinder surface, wherein each circuit loop is phase shifted from an adjacent circuit loop by 90 degrees.

19. The MRI system according to claim 18, further comprising circuitry configured to drive two of the four circuit loops 180 degrees out of phase.

20. The MRI system according to claim 18, further comprising circuitry configured to individually drive each of the four loops.

21. A pediatric magnetic resonance imaging (MRI) system, comprising:
    a magnet-gradient assembly comprising at least one superconducting wire;
    a transmit and/or receive body RF coil configured to image a portion of a patient;
    a pediatric magnetic resonance imaging (MRI) sub-system, comprising:
    an isolette including a patient section for accommodating a patient,
    an MRI compatible infant warming mattress arranged within the patient section,
    the MRI compatible infant warming mattress comprising:
    an interior space; and
    a conduction heating system at least partially arranged in the interior space and configured to conduct heat to the interior space; and
    a conduction cooling system for controlling a temperature of the magnet-gradient assembly via heat transfer through the at least one superconducting wire from the conduction cooling system, wherein the conduction cooling system further comprises a host receptor arranged within the magnet-gradient assembly and housing a cooling medium, wherein the host receptor is cooled by the cryogen-free cooler and has a mass sufficient to maintain system enthalpy over a predetermined time period.

22. The MRI system according to claim 21, wherein the host receptor is held in a vacuum to isolate the cooling medium from the ambient temperature.

23. The MRI system according to claim 21, wherein the cooling medium comprises a primary medium and a secondary medium, each having a specific heat of ≥50 J/Kg·° K and a total heat capacity between 500-1,000 J/Kg at 10-20K.

* * * * *